United States Patent [19]

Müller

[11] Patent Number: 4,535,062
[45] Date of Patent: Aug. 13, 1985

[54] APPARATUS FOR GROWING MICROORGANISMS

[75] Inventor: Hans Müller, Erlenbach, Switzerland

[73] Assignee: Chemap AG, Männedorf, Switzerland

[21] Appl. No.: 464,742

[22] Filed: Feb. 7, 1983

[30] Foreign Application Priority Data

Feb. 12, 1982 [CH] Switzerland ............................ 965/82

[51] Int. Cl.³ ................................................. C12M 1/36
[52] U.S. Cl. ..................................... 435/289; 435/311; 435/312; 435/313; 435/315; 435/316
[58] Field of Search ................ 435/311, 312, 313, 315, 435/316, 314, 243, 41, 289

[56] References Cited

U.S. PATENT DOCUMENTS

| 2,530,814 | 11/1950 | Becze et al. ........................ 435/314 |
| 2,793,166 | 5/1957 | Hatch . |
| 3,114,677 | 7/1961 | Stich . |
| 3,460,810 | 8/1969 | Mueller ............................... 435/316 |
| 3,616,260 | 10/1971 | Müller . |
| 3,809,618 | 5/1974 | Muller ................................ 435/289 |
| 3,847,750 | 12/1974 | Ridgway et al. ................... 435/314 |
| 3,925,165 | 12/1975 | Müller ................................ 435/312 |
| 4,276,384 | 6/1981 | Mueller . |

FOREIGN PATENT DOCUMENTS 0637424 12/1978 U.S.S.R. ............................ 435/313

Primary Examiner—Sam Rosen
Assistant Examiner—William J. Herald
Attorney, Agent, or Firm—Michael J. Striker

[57] ABSTRACT

Growing of microorganisms takes place in a fermenter in which simultaneously products of metabolism are separated and withdrawn by microfiltration with the aid of a diaphragm filter, and a suspension of microorganisms is stirred in the fermenter in the region immediately surrounding the diaphragm filter.

16 Claims, 6 Drawing Figures

APPARATUS FOR GROWING MICROORGANISMS

BACKGROUND OF THE INVENTION

The present invention relates to a method of and an arrangement for growing microorganisms, with simultaneous separation and withdrawal of products of metabolism by ultrafiltration.

Methods and arrangements of the above mentioned general type are known in the art. One known arrangement for growing microorganisms is disclosed in the EP-A-7133. In this arrangement, separation and withdrawal of products of metabolism produced during growing are performed with the aid of a diaphragm filter located in the interior of the fermenter. The diaphragm filter, which is formed as a filter candle, is mounted inside a guide pipe. This arrangement has an improved service life as compared with the previously used arrangements. However, in cases of various media, clogging of the diaphragms and thereby decrease of the filtrate flow in the course of the process take place. This output reduction has evidently the condensation polarization as cause, which cannot be sufficiently overcome by the flow alone.

SUMMARY OF THE INVENTION

Accordingly, it is an object of the present invention to provide a method of and an arrangement for growing microorganisms, in accordance with which a filtration rate of an ultrafilter in a fermenter can be maintained constant over a longer time and with service life improved.

In keeping with these objects and with others which will become apparent hereinafter, one feature of the present invention resides, briefly stated, in a method of and an arrangement for growing microorganisms in accordance with which a suspension accommodated in a fermenter provided with diaphragm filtering means for separating and withdrawing products of metabolism by microfiltration is stirred in the region immediately surrounding the diaphragm filtering means. By stirring the suspension in the region immediately surrounding the diaphragm filtering means or its diaphragm, high concentrations first of all of substances of complex fermentation media cannot take place. The required pressure difference between the concentrate and filtrate sides can be maintained by a vacuum device at the filtrate side and by pressure at the concentrate side. The fermentation under a small negative pressure in many cases is advantageous.

The membrane filter which is formed as a sintered candle with a semipermeable diaphragm thereon is suitable for the inventive method and arrangement. The semipermeable diaphragms are attached as a rule at the outer side and at the inner side of the sintered candle. The candle can be completely packed or formed hollow. The openings of the pores can have a diameter between 0.1 and 50 microns.

The stirring means can include a plurality of baffles. The baffles can surround the diaphragm filter in a manner like a baffle basket. The baffle basket is composed of flat or spiral shaped baffles extending normal or at an acute angle to a drive shaft and mounted on annular disks. The baffles can be additionally provided with stirring arms extending outwardly.

The novel features which are considered characteristic for the invention are set forth in particular in the appended claims. The invention itself, however, both as to its construction and its method of operation, together with additional objects and advantages thereof, will be best understood from the following description of specific embodiments when read in conjunction with the accompanying drawing.

DESCRIPTION OF THE PREFERRED EMBODIMENTS

Figure 1:
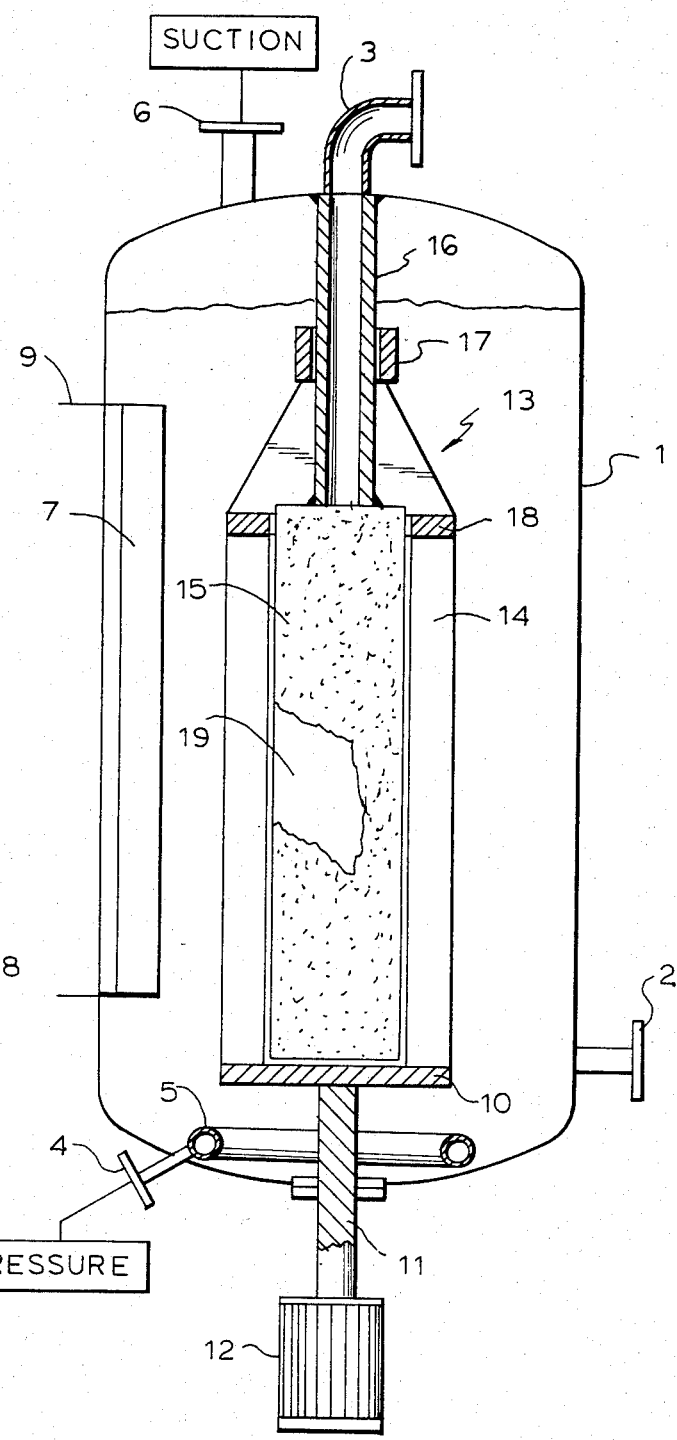
FIG. 1 is a view showing a longitudinal section of a fermenter with a diaphragm filter and a stirring device.

An arrangement for growing microorganisms shown in FIG. 1 is a fermenter which has a container 1 with a pipe 2 for supplying a substrate and a pipe 3 for withdrawing a filtrate. A connecting pipe 4 for supplying air is provided in the lower part of the fermenter, and an annular pipe 5 communicates with the connecting pipe 4 for distribution of the air. A pipe 6 for withdrawing the air is provided in a cover of the container 1. Cooling elements 7 are mounted in the interior of the container 1. They are provided with a pipe 8 for supplying a cooling medium and a pipe 9 for withdrawing the latter.

An annular disk 10 is further provided in the interior of the container 1. It is driven in rotation by a shaft 11 with the aid of an electric motor 12. The annular disk 10 is connected with a stirring device 13. The stirring device 13 includes a plurality of baffles 14. While the lower end of the baffles 14 are connected with the above mentioned annular disk 10, the upper ends of the baffles 14 are connected with a further annular disk 18. The baffles 14 can be flat, spiral-shaped, or formed as a helical impeller.

A tubular diaphragm filter 15 is further located in the interior of the stirring device 13.

The tubular diaphragm filter 15 is arranged inside the stirring device 13 in such way that it is mounted in its upper part on a pipe 16 which serves for withdrawing the filtrate. Guidance of the filter in its upper part is carried out via a support 17. The diaphragm filter 15 can be formed as a porous filter candle which serves as a support, and a semipermeable diaphragm 19 mounted on the filter candle. Sealing of concentrate and permeate is performed in a known manner.

Figure 2:
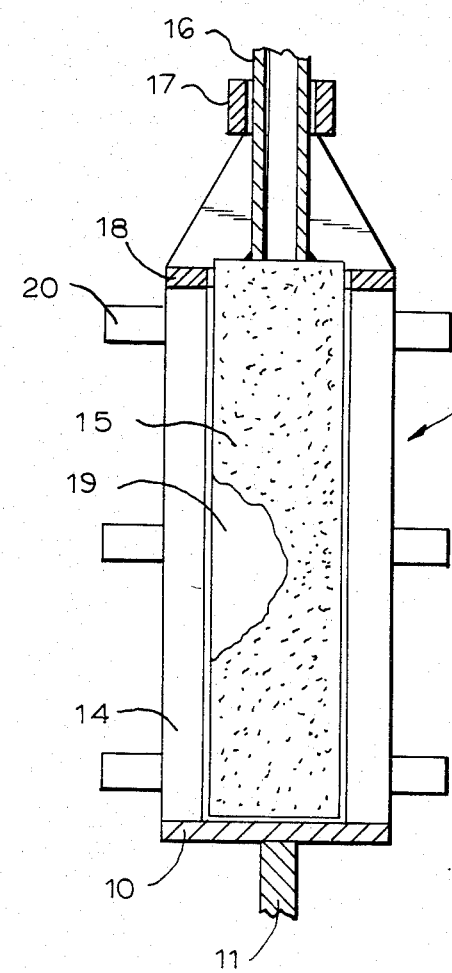
FIG. 2 is a view showing the stirring device with outwardly extending stirring arms.

FIG. 2 shows a stirring device 13 which is provided at its outer side with stirring blades 20. The stirring blades can be used in addition to the inwardly located baffle 14, or alone without the baffles.

Figure 3:
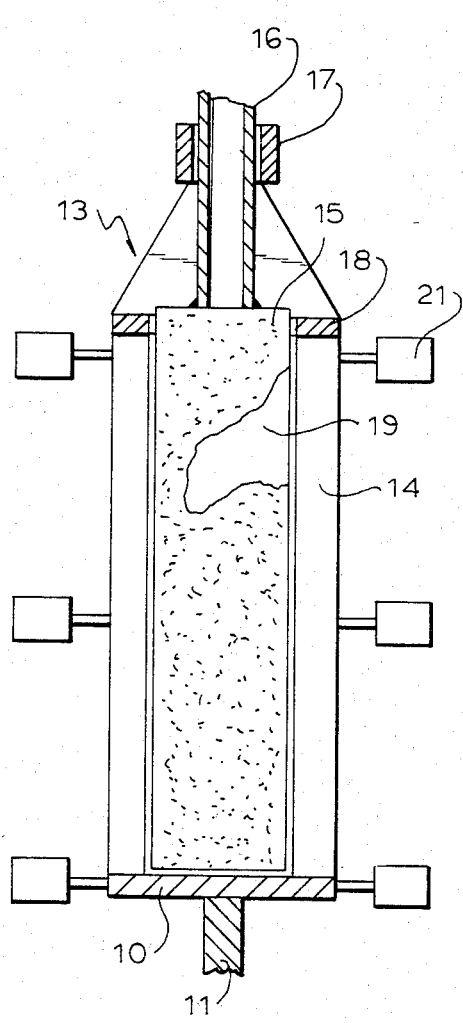
FIG. 3 is a view substantially corresponding to the view of FIG. 2 but showing a different embodiment of the stirring arms.

FIG. 3 shows a stirring arrangement 13 in which a stirring blade 21 is formed as a turbine stirrer. It can be arranged so that it extends normal to the axis of rotation or at an acute angle to the latter.

Figure 4:
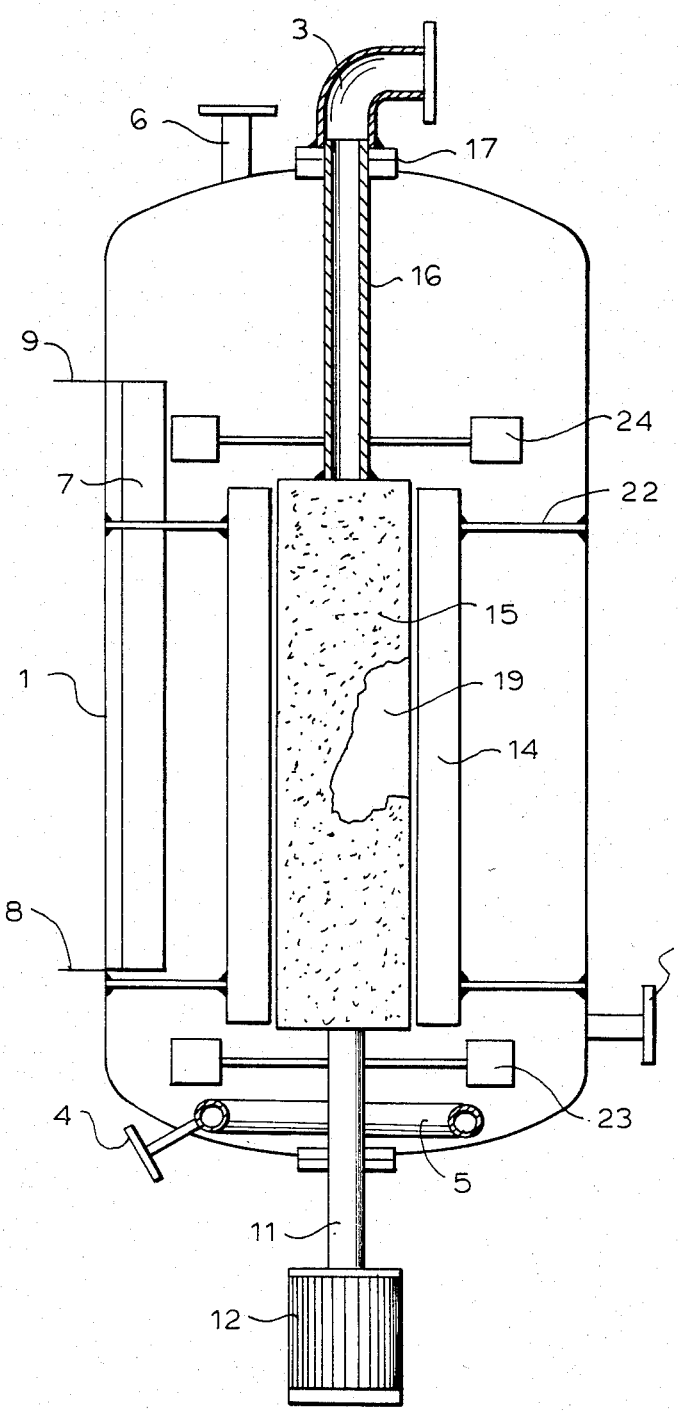
FIG. 4 is a view showing a longitudinal section of the fermenter with a rotatable diaphragm filter, in accordance with the present invention.

FIG. 4 shows an arrangement in which the diaphragm filter 15 is rotatable, whereas baffles 14 are fixedly connected with a wall of the container 1 by mounting elements 22. In this case, an upper support 17 for the diaphragm filter 15 is arranged in the cover of the fermenter. A stirrer 23 can be arranged under the diaphragm filter 15 on a drive shaft 11, and furthermore a stirrer 24 can be arranged above the diaphragm filter on a rotatable pipe 16 for withdrawing the filtrate. Only one of the stirrers 23 or 24, or both these stirrers, can be provided in the inventive arrangement.

Figure 5:
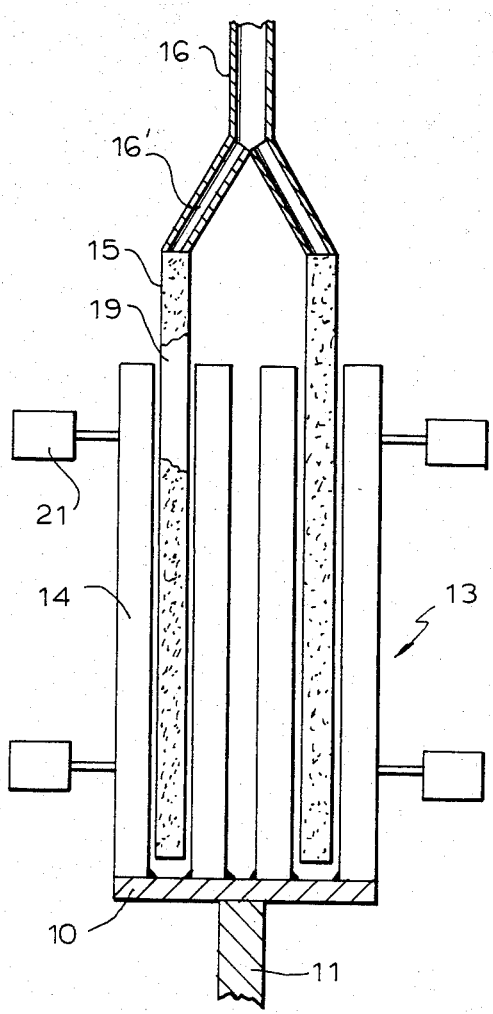
FIG. 5 is a view showing a diaphragm filter of the inventive fermenter with inwardly located rotatable baffle basket.

FIG. 5 shows a diaphragm filter 15 which is mounted on a pipe 16. A semipermeable diaphragm 19 is located in the interior of the sintered pipe. The outer side is sealed. The ultrafiltrate flows from the hollow space of the sintered candle via a collecting pipe 16' into the pipe 16.

Figure 6:
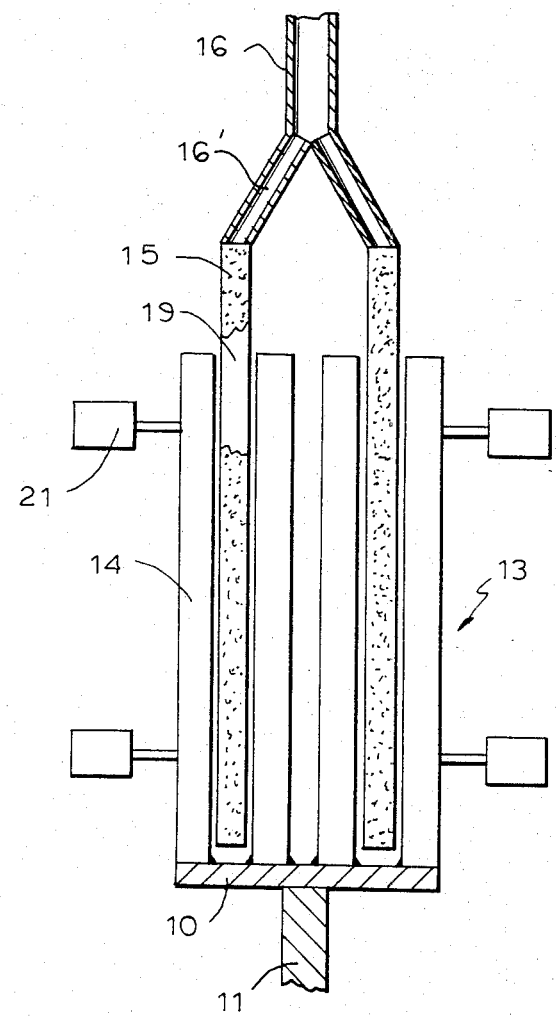
FIG. 6 is a view showing a diaphragm filter of the inventive fermenter surrounded by an anchor stirrer with baffles formed as stirring arms.

FIG. 6 shows an arrangement in which a diaphragm filter 15 provided at both its sides with diaphragms 19 is surrounded by a stirring device 13 formed as a baffle basket. Additional stirring arms can be mounted on the baffles 14.

The arrangement in accordance with the present invention operates in the following manner.

The annular disk 10 is driven in rotation by the shaft 11 and the electric motor 12. The products of metabolism of microorganisms, which are located in a nutrient substrate in the fermenter, leave the fermenter together with the liquid through the diaphragms 19, the hollow space of the porous supporting body of the diaphragm filter 15, and the withdrawing pipe 16. The microorganisms remain in the container 11 of the arrangement. By rotation of the stirring device 13 with the baffles 14 a turbulence takes place in the immediate proximity of the diaphragms 19. This turbulence is so strong that the diaphragms 19 remain free from deposits, despite high concentrations of microorganisms in the fermenter.

It will be understood that each of the elements described above, or two or more together, may also find a useful application in other types of constructions differing from the types described above.

While the invention has been illustrated and described as embodied in a method of and an arrangement for growing of microorganisms with separation of products of metabolism by ultrafiltration, it is not intended to be limited to the details shown, since various modifications and structural changes can be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for growing micro-organisms, comprising:
   a fermenter accommodating a suspension of micro-organisms in a medium for fermentation and growing micro-organisms;
   a diaphragm filter arranged in the interior of said fermenter for separating and withdrawing products of metabolism, said diaphragm filter having an axis and an axially extending peripheral surface radially spaced from said axis; and
   stirring means arranged in the interior of said fermenter between the diaphragm filter and wall of the fermenter for stirring the suspension, said stirring means being located radially outwardly of and immediately near to said peripheral surface of said diaphragm filter and extending axially along said peripheral surface.

2. An apparatus as defined in claim 1, wherein said diaphragm filtering means includes a diaphragm filter with a supporting body which is provided with openings of between 0.1 and 50 microns.

3. An apparatus as defined in claim 1, wherein said stirring means includes a plurality of baffles.

4. An apparatus as defined in claim 3, wherein said baffles have two opposite ends having rings attached thereto.

5. An apparatus as defined in claim 4, wherein said baffles extend in a substantially vertical direction and said opposite ends are upper and lower ends connected with said rings, respectively.

6. An apparatus as defined in claim 3, wherein said baffles of said stirring means are flat baffles.

7. An apparatus as defined in claim 3, wherein said baffles of said stirring means are spiral-shaped baffles.

8. An apparatus as defined in claim 3, wherein said stirring means further has a shaft arranged to rotate said baffles, said baffles being arranged at an acute angle to said shaft.

9. An apparatus as defined in claim 3, wherein said baffles of said stirring means have an outer side and are provided at said outer side with a plurality of stirring arms.

10. An apparatus as defined in claim 1, wherein said diaphragm filter is rotatable.

11. An apparatus as defined in claim 10, wherein said diaphragm filter further includes a diaphragm having two ends and a shaft arranged to rotate said diaphragm, said stirring means including stirring elements located outwardly beyond at least one of said ends of said diaphragm.

12. An apparatus as defined in claim 11, wherein said two ends of said diaphragm are upper and lower ends, said stirring means being located outwardly beyond at least one said upper and lower ends.

13. An apparatus as defined in claim 11, wherein said stirring elements of said stirring means are located outwardly beyond both ends of said diaphragm of said diaphragm filter.

14. An apparatus as defined in claim 10, wherein said fermenter has a wall, said stirring means including a plurality of baffles which surround said diaphragm filter and are fixedly connected with said wall of said fermenter.

15. An apparatus as defined in claim 1, wherein said stirring means includes a plurality of rotatable baffles arranged in the interior of said diaphragm filter.

16. An apparatus as defined in claim 1, wherein said stirring means includes an anchor stirrer having a plurality of stirring elements which are formed by baffles and surround said diaphragm filter.

* * * * *